United States Patent
Stirton et al.

(10) Patent No.: US 6,785,009 B1
(45) Date of Patent: *Aug. 31, 2004

(54) METHOD OF USING HIGH YIELDING SPECTRA SCATTEROMETRY MEASUREMENTS TO CONTROL SEMICONDUCTOR MANUFACTURING PROCESSES, AND SYSTEMS FOR ACCOMPLISHING SAME

(75) Inventors: James Broc Stirton, Austin, TX (US); Kevin R. Lensing, Austin, TX (US); Hormuzdiar E. Nariman, Austin, TX (US); Steven P. Reeves, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 105 days.

This patent is subject to a terminal disclaimer.

(21) Appl. No.: 10/084,987

(22) Filed: Feb. 28, 2002

(51) Int. Cl.$^7$ .............................................. G01B 11/14
(52) U.S. Cl. ...................... 356/625; 356/448; 430/30; 430/396; 438/16
(58) Field of Search ............................. 356/625, 630, 356/60, 601, 445, 448, 600; 430/30, 396; 438/14, 16

(56) References Cited

U.S. PATENT DOCUMENTS

| | | | | |
|---|---|---|---|---|
| 5,607,800 A | * | 3/1997 | Ziger | 430/8 |
| 5,867,276 A | | 2/1999 | McNeil et al. | 356/445 |
| 5,877,860 A | | 3/1999 | Borden | 356/376 |
| 5,880,838 A | | 3/1999 | Marx et al. | 356/351 |
| 6,051,348 A | | 4/2000 | Marinaro et al. | 430/30 |
| 6,081,334 A | | 6/2000 | Grimbergen et al. | 356/357 |
| 6,245,584 B1 | | 6/2001 | Marinaro et al. | 438/14 |
| 6,383,824 B1 | * | 5/2002 | Lensing | 438/14 |
| 6,433,871 B1 | * | 8/2002 | Lensing et al. | 356/450 |
| 6,433,878 B1 | | 8/2002 | Niu et al. | 356/603 |
| 6,479,200 B1 | * | 11/2002 | Stirton | 430/30 |
| 6,529,282 B1 | * | 3/2003 | Stirton et al. | 356/630 |
| 6,582,863 B1 | * | 6/2003 | Stirton et al. | 430/30 |
| 6,597,463 B1 | * | 7/2003 | Singh et al. | 356/630 |
| 6,609,086 B1 | * | 8/2003 | Bao et al. | 702/189 |
| 6,614,540 B1 | * | 9/2003 | Stirton | 356/630 |
| 6,618,149 B1 | * | 9/2003 | Stirton | 356/445 |
| 6,660,542 B1 | * | 12/2003 | Stirton | 438/16 |
| 2002/0135781 A1 | | 9/2002 | Singh et al. | 356/601 |

FOREIGN PATENT DOCUMENTS

| | | | |
|---|---|---|---|
| EP | 0 727 715 A1 | 8/1996 | ............ G03F/7/20 |
| WO | WO 99/45340 | 9/1999 | ........... G01B/11/02 |
| WO | WO 01/23871 A1 * | 4/2001 | .......... G01N/21/95 |

OTHER PUBLICATIONS

Pfitzner et al., "Cost reduction strategies for wafer expenditure," *Miroelectronic Engineering*, 56:61–71, 2001.

* cited by examiner

*Primary Examiner*—Frank G. Font
*Assistant Examiner*—Roy M. Punnoose
(74) *Attorney, Agent, or Firm*—Williams, Morgan & Amerson (57) ABSTRACT

A method of using high yielding spectra scatterometry measurements to control semiconductor manufacturing processes and systems for accomplishing same is disclosed. In one embodiment, the method comprises providing a library comprised of at least one target optical characteristic trace of a grating structure comprised of a plurality of gate stacks, the target trace corresponding to a semiconductor device having at least one desired electrical performance characteristic, providing a substrate having at least one grating structure formed thereabove, the formed grating structure comprised of a plurality of gate stacks, illuminating at least one grating structure formed above said substrate, measuring light reflected off of the grating structure formed above the substrate to generate an optical characteristic trace for the formed grating structure, and comparing the generated optical characteristic trace to the target trace.

25 Claims, 4 Drawing Sheets

METHOD OF USING HIGH YIELDING SPECTRA SCATTEROMETRY MEASUREMENTS TO CONTROL SEMICONDUCTOR MANUFACTURING PROCESSES, AND SYSTEMS FOR ACCOMPLISHING SAME

BACKGROUND OF THE INVENTION

1. Field of the Invention

This invention relates generally to semiconductor fabrication technology, and, more particularly, to a method of using high yielding spectra scatterometry measurements to control semiconductor manufacturing processes, and systems for accomplishing same.

2. Description of the Related Art

There is a constant drive within the semiconductor industry to increase the operating speed of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

Figure 1:
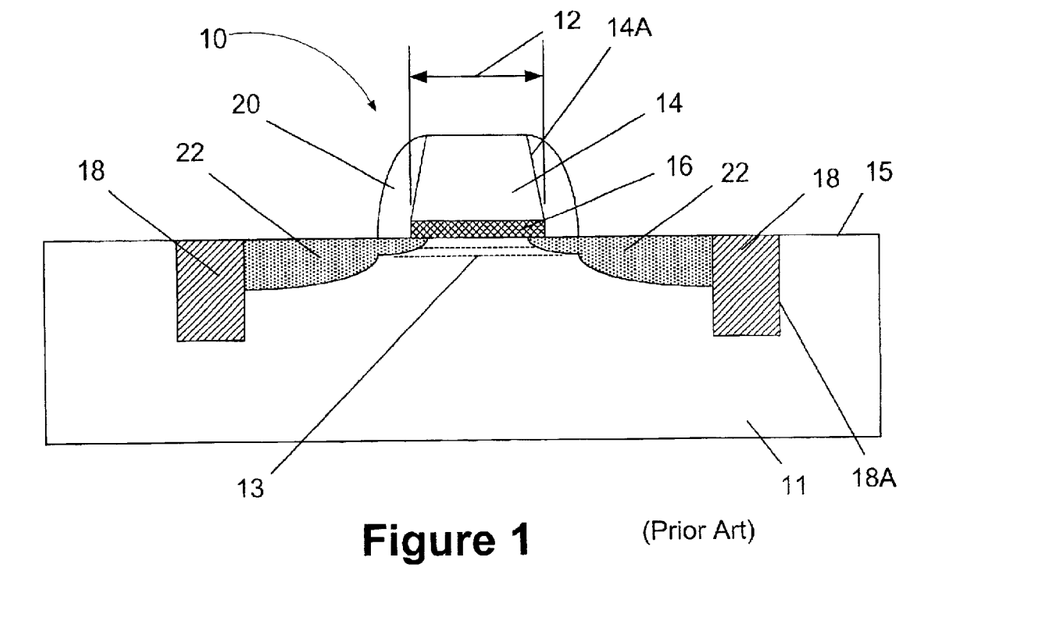
FIG. 1 is a cross-sectional view of an illustrative prior art transistor.

Typically, integrated circuit devices are comprised of hundreds or millions of transistors formed above a semiconducting substrate. By way of background, an illustrative field effect transistor 10, as shown in FIG. 1, may be formed above a surface 15 of a semiconducting substrate or wafer 11 comprised of doped-silicon. The substrate 11 may be doped with either N-type or P-type dopant materials. The transistor 10 may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit device is comprised of a plurality of conductive interconnections, such as conductive lines and conductive contacts or vias, positioned in multiple layers of insulating material formed above the substrate 11.

The gate electrode 14 has a critical dimension 12, i.e., the width of the gate electrode 14 (gate length), that approximately corresponds to the channel length 13 of the device when the transistor 10 is operational. Of course, the critical dimension 12 of the gate electrode 14 is but one example of a feature that must be formed very accurately in modern semiconductor manufacturing operations. Other examples include, but are not limited to, conductive lines, openings in insulating layers to allow subsequent formation of a conductive interconnection, i.e., a conductive line or contact, therein, etc.

One illustrative process flow for forming the illustrative transistor 10 will now be described. Initially, the shallow trench isolation regions 18 are formed in the substrate 11 by etching trenches 18A into the substrate 11 and, thereafter, filling the trenches 18A with an appropriate insulating material, e.g., silicon dioxide. Next, a gate insulation layer 16 is formed on the surface 15 of the substrate 11 between the trench isolation regions 18. This gate insulation layer 16 may be comprised of a variety of materials, but it is typically comprised of a thermally grown layer of silicon dioxide. Thereafter, the gate electrode 14 for the transistor 10 is formed by forming a layer of gate electrode material, typically polysilicon, above the gate insulation layer 16, and patterning the layer of gate electrode material using known photolithography and etching techniques to thereby define the gate electrode 14. The sidewalls 14A of the gate electrode 14 tend to flare outwardly a very small amount. Of course, millions of such gate electrodes are being formed across the entire surface of the substrate 11 during this patterning process. The source/drain regions 22 and the sidewall spacers 20 are then formed using a variety of known techniques. Additionally, metal silicide regions (not shown) may be formed above the gate electrode 14 and the source/drain regions 18.

After an integrated circuit device is fabricated, it is subjected to several electrical tests to insure its operability and to determine its performance capabilities. The performance capabilities of integrated circuit products, e.g., microprocessors, may vary quite a bit despite great efforts to insure that all of the integrated circuit products are fabricated with the same process steps. For example, the operating frequency of microprocessors may vary over a given range. Many factors, or interrelationships among various factors, may be the cause of such variations, and such causes may be difficult to determine. Variations in the performance level of the integrated circuit devices may be problematic for a variety of reasons. For example, at least in the case of microprocessors, higher performance microprocessors tend to sell for higher prices in the marketplace, while lower performance microprocessors tend to sell for lesser prices. Thus, all other things being equal, a microprocessor manufacturer would like to be able to produce as many high performance microprocessors as possible. Stated another way, an integrated circuit manufacturer would like to be able to consistently and reliably mass produce integrated circuit devices at the very highest performance level the product design and manufacturing equipment will allow.

The present invention is directed to a method and systems that may solve, or at least reduce, some or all of the aforementioned problems.

SUMMARY OF THE INVENTION

The present invention is generally directed to a method of using high yielding spectra scatterometry measurements to control semiconductor manufacturing processes, and a system of accomplishing same. In one illustrative embodiment, the method comprises providing a library comprised of at least one target optical characteristic trace of a grating structure comprised of a plurality of gate stacks, the target trace corresponding to a semiconductor device having at least one desired electrical performance characteristic, providing a substrate having at least one grating structure formed thereabove, the formed grating structure comprised of a plurality of gate stacks, illuminating at least one grating structure formed above said substrate, measuring light reflected off of the grating structure formed above the substrate to generate an optical characteristic trace for the formed grating structure, and comparing the generated optical characteristic trace to the target trace.

The present invention is also directed to various systems for accomplishing the illustrative methods described herein. In one embodiment, the system is comprised of a scatterometry tool, a process tool and a controller. The scatterometry tool is adapted to make scatterometric measurements of a grating structure comprised of a plurality of gate stacks and generate an optical characteristic trace for the grating structure. The scatterometry tool may be further used to compare the generated optical characteristic trace to a target optical characteristic trace that is determined based upon electrical test data for a semiconductor device. If a deviation exists between the generated trace and the target trace, the controller may then be used to control one or more parameters of one or more processes to be performed on the substrate comprised of the deficient or sub-standard gate stacks.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to a method of using high yielding spectra scatterometry measurements to control semiconductor manufacturing processes, and systems for accomplishing same. As will be readily apparent to those skilled in the art upon a complete reading of the present application, the present method is applicable to a variety of technologies, e.g., NMOS, PMOS, CMOS, etc., and it is readily applicable to a variety of devices, including, but not limited to, logic devices, memory devices, etc.

Figure 2:
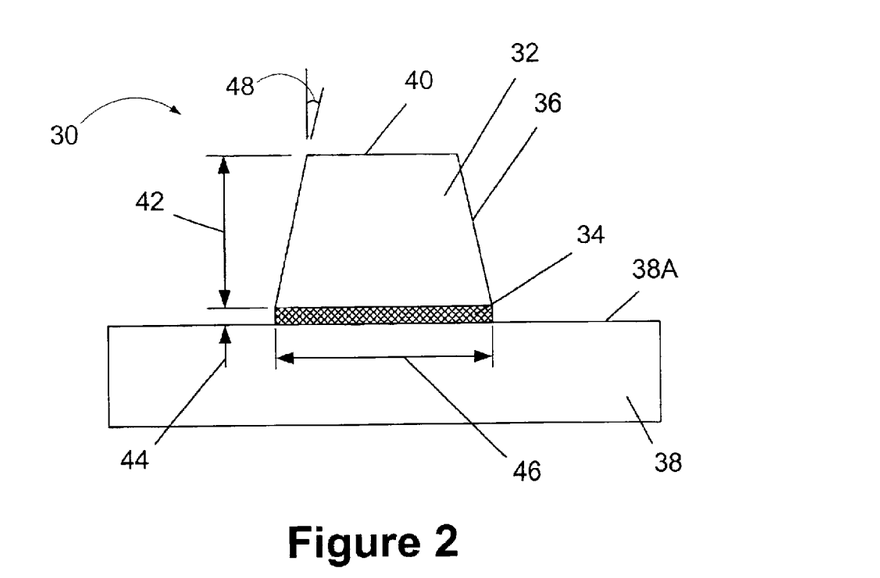
FIG. 2 is a cross-sectional view of an illustrative gate stack.

FIG. 2 depicts an enlarged view of an illustrative gate stack 30. As shown therein, the gate stack 30 is comprised of a gate electrode 32 and a gate insulation layer 34 formed above a semiconducting substrate or wafer 38. The gate electrode 32 has sidewalls 36 and a top surface 40. The gate electrode 32 has a thickness 42, and the gate insulation layer 34 has a thickness 44. The gate electrode 32 defines a critical dimension 46. The profile of the gate electrode 32 is depicted as having a trapezoidal cross-section due to the fact that there is generally some slight degree of tapering of the sidewalls 36 during the manufacturing process. That is, the sidewalls 36 of the gate electrode 32 are slightly tapered, as represented by the angle 48, on the order of 2–3 degrees with respect to a line normal to the surface 38A of the substrate 38 due to the nature of the etching processes employed in forming the gate electrode 32. Ideally, the sidewalls 36 have essentially no taper, but current etching processes cannot readily and repeatedly produce such ideal structures. In some embodiments, a layer of metal silicide may ultimately be formed above the gate electrode 32, although that structure is not depicted in the attached drawings.

The gate electrode 32 and the gate insulation layer 34 may be comprised of a variety of materials, and they may be formed using a variety of known processing techniques. In one illustrative embodiment, the gate insulation layer 34 is comprised of a thermally grown layer of silicon dioxide having a thickness 44 ranging from approximately 1.5–5 nm, and the gate electrode 32 is comprised of a doped polysilicon, and it has a thickness 42 that ranges from approximately 150–400 nm.

Figure 3A:
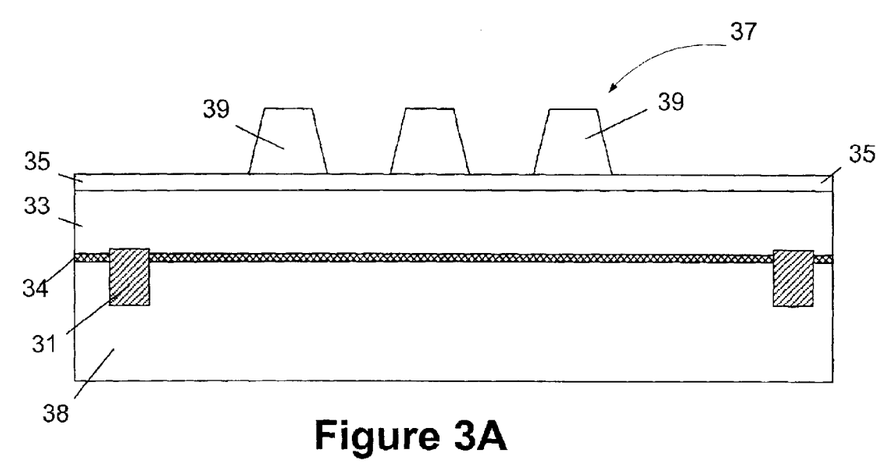
FIGS. 3A–3B depict an illustrative process flow for forming an illustrative gate stack.
Figure 3B:
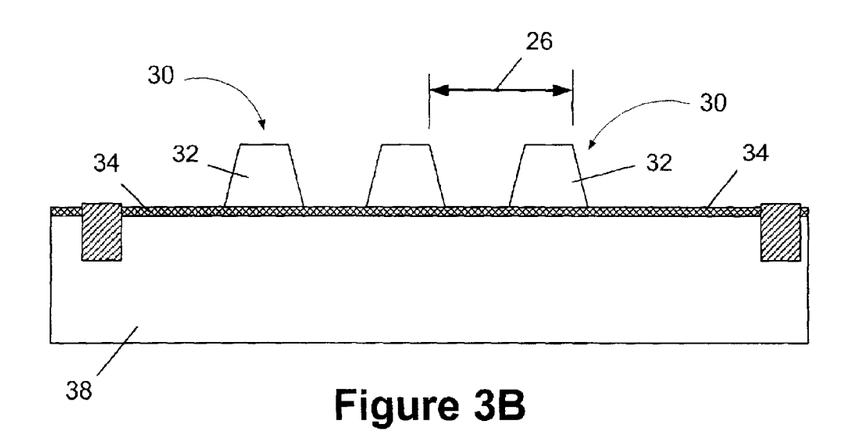

In general, one or more characteristics of the gate stack 30 may have profound impact on the performance characteristics of the resulting integrated circuit device. For example, the critical dimension 46 is one very important factor in determining device performance levels. Thus, great attention is given to controlling the critical dimension 46 of the gate electrode 32. However, the complete gate stack 30 is the result of many process steps that may impact many variables or characteristics of the gate stack 30, which may, in turn, have an impact on device performance. For example, a typical process flow for forming the gate stack 30 will now be described with reference to FIGS. 3A–3B. As shown therein, a trench isolation region 31 is formed in the substrate 38. Next, the gate insulation layer 34 may be thermally grown in a furnace, and a layer of polysilicon 33 may be deposited above the gate insulation layer 34 using a chemical vapor deposition ("CVD") process. The layer of polysilicon 33 may be doped with an appropriate dopant material, i.e., an N-type dopant for an NMOS device, a P-type dopant for a PMOS device. This may be accomplished by performing an ion implant process after the layer of polysilicon 33 is formed or by introducing the appropriate dopant material during the deposition process performed to form the layer of polysilicon 33. Thereafter, in some cases, an anti-reflective coating layer 35, sometimes referred to as an ARC or BARC layer, comprised of, for example, silicon nitride, is formed above the layer of polysilicon 33 by a deposition process, such as a CVD process. Next, a patterned layer of photoresist 37, comprised of photoresist features 39, may be formed above the anti-reflecting coating layer 35 (or layer of polysilicon 33 if the ARC layer 35 is not present) using known photolithographic methods and equipment. Then, one or more etching processes may be performed using the patterned layer of photoresist 37 as a mask to result in the definition of a plurality of gate stacks 30, as shown in FIG. 3B. For example, an initial timed, anisotropic etching process may be used to etch through approximately 75% of the thickness of the layer of polysilicon 33. Thereafter, a second, endpoint etching process that is substantially isotropic in nature may be used to remove the remaining portion of the layer of polysilicon 33. The second etching process is intended to be highly selective with respect to the material comprising the gate insulation layer 34 to insure integrity of the gate insulation layer 34.

From the foregoing, it can be understood that a variety of process steps are frequently performed in forming a gate stack 30 for an integrated circuit device. To some degree, the process steps are interrelated in that they may have an impact on the resulting characteristics of the gate stack 30, which may, in turn, have an impact on the ultimate performance capability of the finished integrated circuit device. For example, the thickness 44 of the gate insulation layer 34 and the thickness 42 of the gate electrode 32 may vary due to the nature of the processes used to form those components. The level of doping within the gate electrode 32, as well as its distribution throughout the gate electrode 32, may vary due to the manner in which dopants are introduced into the gate electrode 32, and heating of the gate electrode 32 in subsequent process operations. The thickness of the ARC layer 35 (if used) may also have an impact on the formation of the gate stack 30. For example, the temperature of the deposition process used to form the ARC layer 35 may act to, in effect, cause unwanted migration of dopant atoms within the layer of polysilicon 33. The quality of the patterned layer of photoresist 37 may also impact the ability to form the gate electrode 32 to the desired critical dimension 46 and profile. Lastly, variations in etching processes may lead to problems such as flaring or undercutting the gate electrode.

As a result of all of the possible interrelated factors that may impact the structure, character and/or quality of the gate stack 30, it is difficult to determine what factor, or combination of factors, of the gate stack 30 need to be controlled to achieve the ultimate objective, i.e., to increase the yield of integrated circuit devices with elevated device performance characteristics. As used herein, the term "gate stack" shall be understood to comprise at least the gate insulation layer 34 and the gate electrode 32. However, in some cases, it may include additional structures, e.g., an ARC layer. According to the present invention, scatterometry techniques and electrical test data of production devices are used to establish a target optical characteristic trace that is representative of a gate stack 30 that exhibits increased device performance characteristics. This target trace may then be used for a variety of purposes, such as to modify or control processes used to form gate stacks 30 on subsequently processed substrates such that optical characteristic traces of the resulting gate stacks 30 correspond to or are closely matched with the target trace. Another example of the use of such a target trace would be to determine what process operations (or parameters) may need to be adjusted to improve performance characteristics. Such information may also be used to detect gate stack 30 structures that deviate from the target trace and, if appropriate and possible, take corrective action to remedy the problem.

Figure 4A:
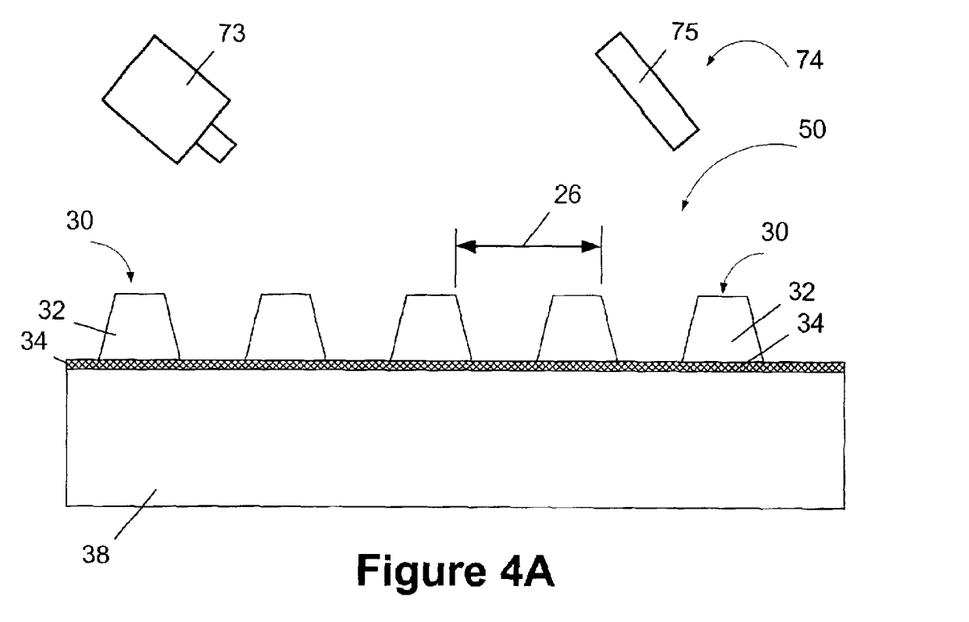
FIGS. 4A–4B depict an illustrative grating structure comprised of a plurality of gate stacks, and a scatterometry tool for illuminating such grating structures in accordance with one aspect of the present invention.
Figure 4B:
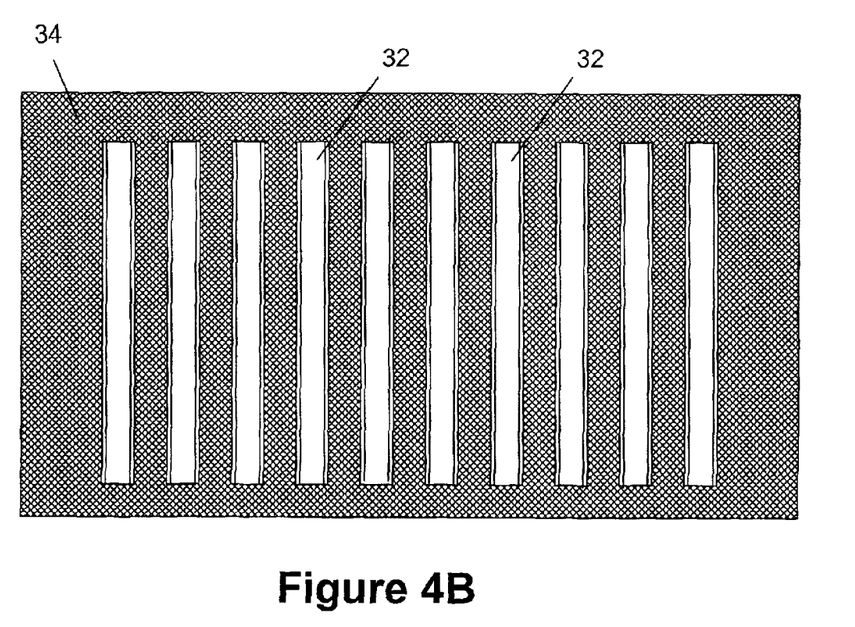

In one embodiment, as shown in FIGS. 4A–4B, the present invention involves the formation of a plurality of gate stacks 30 to define a grating structure 50. The gate stacks 30 comprising the grating structure 50 may have a pitch 26 that, in one illustrative embodiment, varies from approximately 400–1000 nm. The grating structure 50 may be formed in a scribe line of the wafer 38, and the grating structure 50 may be formed at the same time the gate stacks 30 are being formed for production devices formed on the wafer 38. A plurality of such grating structures 50 may be formed at various locations across a surface of a wafer 38. Depending upon the type of integrated circuit device under construction, and/or as a matter of design choice, the grating structure(s) 50 may be comprised of gate stacks 30 that can be part of actual production integrated circuit devices. For example, for memory devices, the gate stacks 30 comprising the grating structure 50 may be gate stacks 30 that are part of the completed memory device. To the extent the grating structure 50 is formed in a scribe line of the wafer 38, it will be assumed to be representative of gate stacks 30 formed on actual production devices. The size, shape and configuration of the grating structure 50 may be varied as a matter of design choice. For example, the grating structure 50 may be formed in an area having approximate dimensions of 100 $\mu$m×120 $\mu$m, and it may be comprised of approximately 500–1500 gate stacks 30 (depending upon the selected pitch).

Figure 5:
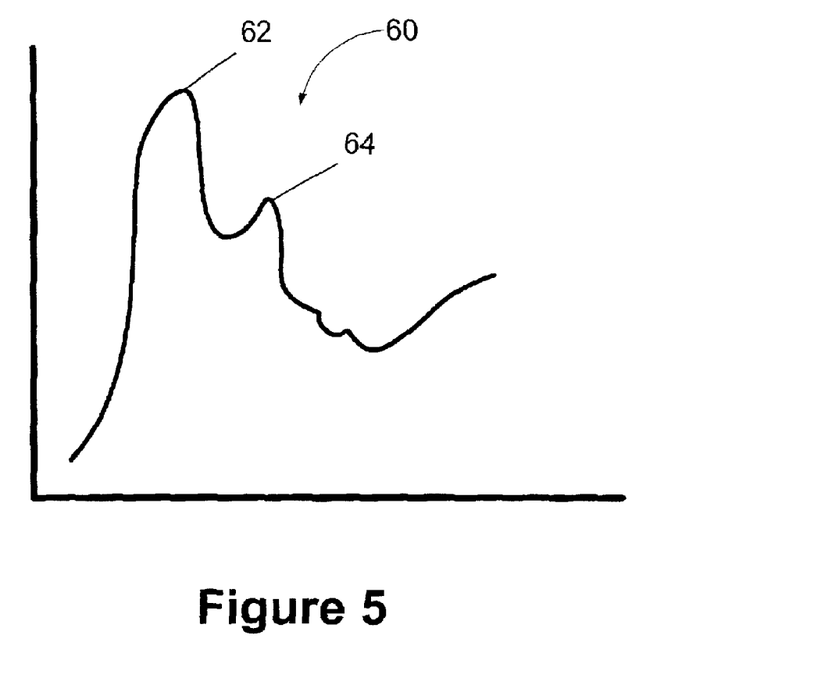
FIG. 5 is an illustrative example of a target optical characteristic trace in accordance with one embodiment of the present invention.

Also depicted in FIG. 4A is an illustrative scatterometry tool 74 comprised of a representative light source 73 and a detector 75. Initially, an optical characteristic trace of the grating structure 50 will be generated after the gate stacks 30 are formed. A plurality of traces for each of a plurality of grating structures 50 may be generated from one or more wafers. Thereafter, additional processing operations may be performed to complete the formation of the integrated circuit devices in the production die area of the wafer 38. Then, various electrical tests may be performed on the completed integrated circuit devices to determine various electrical performance characteristics of the completed device. For example, parameters such as drive current ($I_{d,Sat}$) or operating frequency may be determined for the completed devices. Ultimately, the optical characteristic traces of the grating structures 50 will be correlated with the electrical test data to determine a target optical characteristic trace that correlates with the increased device performance characteristics as indicated by the electrical test data. That is, the optical characteristic trace or traces associated with the completed devices exhibiting the desired increased performance characteristics, e.g., the highest operating frequency, may be determined to define an illustrative target trace 60, as depicted in FIG. 5. The target trace 60 may be a plot of light intensity versus wavelength or incident angle. This correlation between the optical characteristic traces and the test data may be established by using known statistical analysis techniques.

The target trace 60 may exhibit certain characteristics that may be readily recognized, such as the relatively sharp peak 62 or the combination of upward peaks 62, 24 as shown in FIG. 5. Of course, it should be understood that the target trace 60 depicted in FIG. 5 is illustrative in nature and that, in practice, the shape of this target trace 60 may vary depending on a variety of factors, e.g., the size or composition of the gate stack 30, the type of device under construction, etc. Through use of the target trace 60 that is correlated with electrical test data many of the unknown variations or interrelationships between the various process steps and materials used to form the gate stack 30 may be accounted for by producing gate stacks 30 that exhibit the same, or very closely match, the characteristics of the target trace 30. That is, the focus is on the ultimate objective—increasing the yield of devices exhibiting increased performance characteristics—and measuring all process changes or modifications against this standard. Of course, the particular electrical characteristic(s) that are correlated with the optical characteristic traces to produce the target trace 60 may vary depending upon the device under construction. Thus, the particular electrical characteristics identified herein should not be considered a limitation of the present invention unless such limitations are clearly set forth in the appended claims.

In another embodiment, the target trace 60 may be used in various engineering experiments to determine the impact that modification of certain process parameters have on producing gate stacks 30 having a generated scatterometric trace that approximates the target trace 60. For example, such engineering experiments would focus on whether the process change under investigation would cause a change in the height of the peak 62 of the target trace 60 or eliminate or reduce the relationship between the peaks 62, 64. In short, all of the engineering experimentation would be measured against the target trace 60, as it is representative of completed devices that exhibit the increased performance characteristics.

In yet another embodiment, the target trace 60 of the present invention may be used to determine corrective actions to be taken in the manufacture of integrated circuit devices. As stated previously, the manufacture of integrated circuit devices involves many process steps involving very complex process tools, e.g., deposition tools, etching tools, ion implant tools, etc. Despite best efforts to control these processes, undesirable process variations will likely continue to occur. As a result, the characteristics of the gate stacks 30 formed will also tend to vary to some degree, e.g., the profile or critical dimension of the gate electrode 32 may vary, the thickness of the gate electrode 32 or the gate insulation layer 34 may vary, etc. By generating an optical characteristic trace of a grating structure 50 comprised of such gate stacks 30 and comparing the generated trace to the target trace 60, it may be evident that, as manufactured, the subject gate stacks 30 will produce integrated circuit devices that exhibit lower levels of performance. In some situations, corrective action may be taken. For example, a generated trace for the subject gate stacks 30 may not match the target trace 60 because the critical dimension 46 of the gate electrode 32 is larger than desired. Irrespective of the cause of the deviation from the target trace 60, the parameters of one or more of the ion implant processes used to form source/drain regions for the finished device may be modified in an effort to compensate for what would otherwise be a sub-standard device. For example, the implant dose on such devices may be increased in an effort to increase the performance level.

Figure 6:
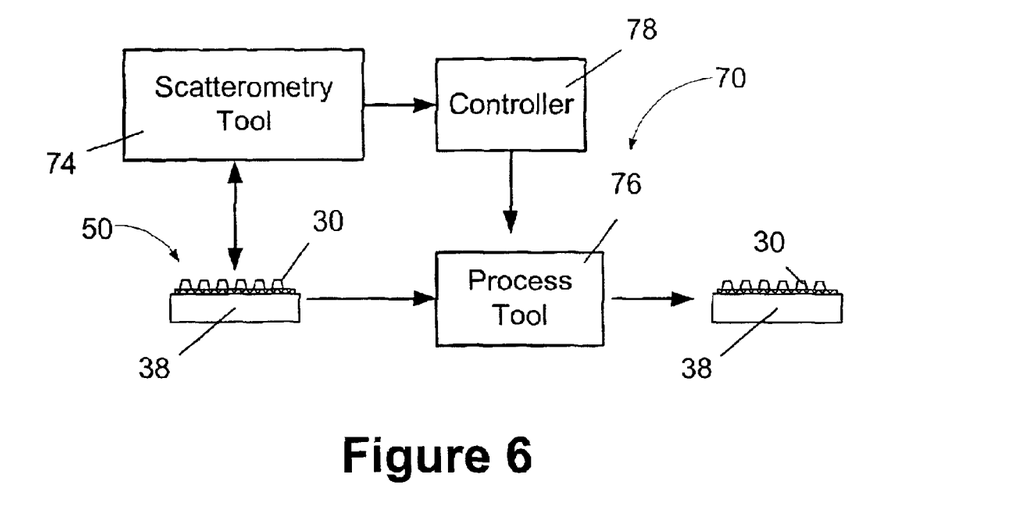
FIG. 6 depicts an illustrative embodiment of a system in accordance with one embodiment of the present invention.

An illustrative system 70 that may be used in one embodiment of the present invention is shown in FIG. 6. The system 70 is comprised of a scatterometry tool 74, a process tool 76, and a controller 78. As indicated in FIG. 6, the wafer 38 is representative of one or more wafers 38 that have a grating structure 50 comprised of a plurality of gate stacks 30 formed thereabove. The representative wafer 38 is to be subjected to additional processing in the process tool 76. The process tool 76 may be any type of process tool commonly found in semiconductor manufacturing operations, e.g., an ion implant tool, an etch tool, a deposition tool, a furnace, etc.

A variety of scatterometry tools 74 may be used with the present invention, e.g., so-called 2θ-type systems and lens-type scatterometry tools. The scatterometry tool 74 may use white light, or some other wavelength or combination of wavelengths, depending on the specific implementation. Typically, the scatterometry tool 74 will generate an incident beam that has a wide spectral composition and wherein the intensity of the light changes slowly in comparison to changes in wavelength. The angle of incidence of the light may also vary, depending on the specific implementation. The optical characteristic traces generated by the scatterometry tool 74 may be based upon a comparison of light intensity to wavelength (for white light, fixed angle type scatterometry tools) or a comparison of intensity to incident angle (for angle resolved systems that use a single light source).

The scatterometry tool 74 may measure one or more grating structures 50 on a given wafer in a lot or even generate an optical characteristic trace for each grating structure 50 in the lot, depending on the specific implementation. Moreover, the optical characteristic traces from a sample of the grating structures 50 may be averaged or otherwise statistically analyzed. The scatterometry tool 74 (or some other controller resident within the manufacturing plant, e.g., controller 78) compares the generated optical characteristic trace (i.e., individual or averaged) to the target trace 60. The comparison between the generated optical characteristic trace and the target trace 60 may be made using known analytical techniques, e.g., mean square error. If there is a close match or approximation to the target trace 60, the controller 78 may record this fact and, if desired, issue a confirmatory message to a supervisor computer or operator. If there is a significant deviation between the measured optical characteristic trace(s) for the grating structure(s) 50, then the controller 78 may take various actions. For example, the controller 78 may identify the subject wafer 38, or lots of wafers 38, as wafers that are likely to produce lower performance integrated circuit devices. The controller 78 may also issue a notification to a supervisory computer or operating personnel that it has identified the sub-standard wafer. The controller 78 may also issue command to the process tool 76 to modify one or more parameters of the process operation to be performed on the identified wafers 38 in the process tool 76 in an effort to compensate for the deficiencies in the gate stacks 30, as determined by the comparison between the generated optical characteristic trace and the target trace 60.

Control equations may be employed to adjust the operating recipe of the process tool 76 in situations where the methods described herein indicate that an adjustment is warranted. The control equations may be developed empirically using commonly known linear or non-linear techniques. The controller 78 may automatically control the operating recipes of the process tool 76 us ed to perform one or more process operations on the identified, sub-standard wafers.

In the illustrated embodiments, the controller 78 is a computer programmed with software to implement the functions described herein. Moreover, the functions described for the controller 78 may be performed by one or more controllers spread through the system. For example, the controller 78 may be a fab level controller that is used to control processing operations throughout all or a portion of a semiconductor manufacturing facility. Alternatively, the controller 78 may be a lower level computer that controls only portions or cells of the manufacturing facility. Moreover, the controller 78 may be a stand-alone device, or it may reside on the process tool 76. However, as will be appreciated by those of ordinary skill in the art, a hardware controller (not shown) designed to implement the particular functions may also be used.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 78, as described, is the Catalyst system offered by KLA Tencor, Inc. The Catalyst system uses Semiconductor Equipment and Materials International (SEMI) Computer Integrated Manufacturing (CM) Framework compliant system technologies, and is based on the Advanced Process Control (APC) Framework. CIM (SEMI E81-0699—Provisional Specification for CIM Framework Domain Architecture) and APC (SEMI E93-0999—Provisional Specification for CIM Framework Advanced Process Control Component) specifications are publicly available from SEMI.

The present invention is generally directed to a method of using high yielding spectra scatterometry measurements to control semiconductor manufacturing processes, and systems for accomplishing same. In one illustrative embodiment, the method comprises providing a library comprised of at least one target optical characteristic trace of a grating structure comprised of a plurality of gate stacks, the target trace corresponding to a semiconductor device having at least one desired electrical performance characteristic, providing a substrate having at least one grating structure formed thereabove, the formed grating structure comprised of a plurality of gate stacks, illuminating at least one grating structure formed above said substrate, measuring light reflected off of the grating structure formed above the substrate to generate an optical characteristic trace for the formed grating structure, and comparing the generated optical characteristic trace to the target trace.

The present invention is also directed to various systems for accomplishing the illustrative methods described herein. In one embodiment, the system 70 is comprised of a scatterometry tool 74, a process tool 76 and a controller 78. The scatterometry tool 74 is adapted to make scatterometric measurements of a grating structure 50 comprised of a plurality of gate stacks 30 and generate an optical characteristic trace for the grating structure 50. The scatterometry tool 74 may be further used to compare the generated optical characteristic trace to a target optical characteristic trace that is determined based upon electrical test data for a semiconductor device. If a deviation exists between the generated trace and the target trace, the controller 78 may then be used to control one or more parameters of one or more processes to be performed on the substrate comprised of the deficient or sub-standard gate stacks 30.

Through use of the present invention, better process control may be achieved in modern integrated circuit manufacturing facilities. Additionally, the present invention may enable more precise formation of gate stacks employed in integrated circuit devices, thereby improving device performance and increasing production yields.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
   providing a library comprised of at least one target optical characteristic trace of a grating structure comprised of a plurality of gate stacks, said target trace corresponding to a semiconductor device having at least one desired electrical performance characteristic;
   providing a substrate having at least one grating structure formed thereabove, said formed grating structure comprised of a plurality of gate stacks;

illuminating said at least one grating structure formed above said substrate;

measuring light reflected off of said at least one grating structure formed above said substrate to generate an optical characteristic trace for said formed grating structure; and comparing said generated optical characteristic trace to said target trace.

2. The method of claim 1, wherein providing a library comprised of at least one target optical characteristic trace of a grating structure comprised of a plurality of gate stacks, said target trace corresponding to a semiconductor device having at least one desired electrical performance characteristic, comprises:

generating a plurality of optical characteristic traces for a plurality of grating structures comprised of a plurality of gate stacks;

generating electrical test data for at least one semiconductor device; and correlating at least one of said plurality of optical characteristic traces with said electrical test data to determine a target optical characteristic trace that corresponds to a semiconductor device having at least one desired electrical performance characteristic.

3. The method of claim 1, further comprising adjusting at least one parameter of at least one process used to form gate stack on a subsequently processed wafer based upon said comparison of said generated trace and said target trace.

4. The method of claim 1, further comprising adjusting at least one parameter of at least one process operation to be performed on said provided substrate based upon a deviation between said generated trace and said target trace.

5. The method of claim 1, wherein providing a substrate having at least one grating structure formed thereabove comprises providing a substrate having at least one grating structure formed in a scribe line of said substrate.

6. The method of claim 1, wherein providing a substrate having at least one grating structure formed thereabove comprises providing a substrate having at least one grating structure formed in a production die formed above said substrate.

7. The method of claim 1, wherein providing a substrate having at least one grating structure formed thereabove comprises providing a substrate having a plurality of grating structures formed thereabove.

8. The method of claim 1, wherein said grating structure formed above said provided substrate is formed in an area having dimensions of approximately 100×120 μm.

9. The method of claim 1, wherein said at least one desired electrical performance characteristic comprises at least one of a drive current and an operating frequency.

10. A method, comprising:

providing a library comprised of at least one target optical characteristic trace of a grating structure comprised of a plurality of gate stacks, said target trace corresponding to a semiconductor device having at least one desired electrical performance characteristic;

providing a silicon substrate having at least one grating structure formed thereabove, said formed grating structure comprised of a plurality of gate stacks;

illuminating said at least one grating structure formed above said substrate;

measuring light reflected off of said at least one grating structure formed above said substrate to generate an optical characteristic trace for said formed grating structure;

comparing said generated optical characteristic trace to said target trace; and adjusting at least one parameter of at least one process used to form a gate stack on a subsequently processed wafer based upon said comparison of said generated trace and said target trace.

11. The method of claim 10, wherein providing a library comprised of at least one target optical characteristic trace of a grating structure comprised of a plurality of gate stacks, said target trace corresponding to a semiconductor device having at least one desired electrical performance characteristic, comprises:

generating a plurality of optical characteristic traces for a plurality of grating structures comprised of a plurality of gate stacks;

generating electrical test data for at least one semiconductor device; and correlating at least one of said plurality of optical characteristic traces with said electrical test data to determine a target optical characteristic trace that corresponds to a semiconductor device having at least one desired electrical performance characteristic.

12. The method of claim 10, further comprising adjusting at least one parameter of at least one process operation to be performed on said provided substrate based upon a deviation between said generated trace and said target trace.

13. The method of claim 10, wherein providing a substrate having at least one grating structure formed thereabove comprises providing a substrate having at least one grating structure formed in a scribe line of said substrate.

14. The method of claim 10, wherein providing a substrate having at least one grating structure formed thereabove comprises providing a substrate having at least one grating structure formed in a production die formed above said substrate.

15. The method of claim 10, wherein providing a substrate having at least one grating structure formed thereabove comprises providing a substrate having a plurality of grating structures formed thereabove.

16. The method of claim 10, wherein said grating structure formed above said provided substrate is formed in an area having dimensions of approximately 100×120 μm.

17. The method of claim 10, wherein said at least one desired electrical performance characteristic comprises at least one of a drive current and an operating frequency.

18. A method, comprising:

providing a library comprised of at least one target optical characteristic trace of a grating structure comprised of a plurality of gate stacks, said target trace corresponding to a semiconductor device having at least one desired electrical performance characteristic;

providing a silicon substrate having at least one grating structure formed thereabove, said formed grating structure comprised of a plurality of gate stacks;

illuminating said at least one grating structure formed above said substrate;

measuring light reflected off of said at least one grating structure formed above said substrate to generate an optical characteristic trace for said formed grating structure;

comparing said generated optical characteristic trace to said target trace; and adjusting at least one parameter of at least one process operation to be performed on said provided substrate based upon a deviation between said generated trace and said target trace.

19. The method of claim 18, wherein providing a library comprised of at least one target optical characteristic trace of a grating structure comprised of a plurality of gate stacks, said target trace corresponding to a semiconductor device having at least one desired electrical performance characteristic, comprises:

generating a plurality of optical characteristic traces for a plurality of grating structures comprised of a plurality of gate stacks;

generating electrical test data for at least one semiconductor device; and correlating at least one of said plurality of optical characteristic traces with said electrical test data to determine a target optical characteristic trace that corresponds to a semiconductor device having at least one desired electrical performance characteristic.

20. The method of claim 18, further comprising adjusting at least one parameter of at least one process used to form a gate stack on a subsequently processed wafer based upon said comparison of said generated trace and said target trace.

21. The method of claim 18, wherein providing a substrate having at least one grating structure formed thereabove comprises providing a substrate having at least one grating structure formed in a scribe line of said substrate.

22. The method of claim 18, wherein providing a substrate having at least one grating structure formed thereabove comprises providing a substrate having at least one grating structure formed in a production die formed above said substrate.

23. The method of claim 18, wherein providing a substrate having at least one grating structure formed thereabove comprises providing a substrate having a plurality of grating structures formed thereabove.

24. The method of claim 18, wherein said grating structure formed above said provided substrate is formed in an area having dimensions of approximately 100×120 μm.

25. The method of claim 18, wherein said at least one desired electrical performance characteristic comprises at least one of a drive current and an operating frequency.

* * * * *